US006229059B1

(12) United States Patent
Motz

(10) Patent No.: US 6,229,059 B1
(45) Date of Patent: May 8, 2001

(54) PROCESS FOR THE PRODUCTION OF 1, 2-DICHLOROETHANE

(75) Inventor: Joachim Motz, Kelkheim (DE)

(73) Assignee: Krupp Uhde GmbH, Dortmund (DE)

( * ) Notice: Subject to any disclaimer, the term of this patent is extended or adjusted under 35 U.S.C. 154(b) by 0 days.

(21) Appl. No.: 09/498,003

(22) Filed: Feb. 4, 2000

(30) Foreign Application Priority Data

Feb. 6, 1999 (DE) ................................................ 199 04 836

(51) Int. Cl.$^7$ .................................................... C07C 17/02
(52) U.S. Cl. ............................................ 570/247; 570/262
(58) Field of Search ..................................... 570/247, 262

(56) References Cited

U.S. PATENT DOCUMENTS 4,760,207 * 7/1988 Cowfer .................................. 570/243

FOREIGN PATENT DOCUMENTS

1422303 * 1/1976 (GB) .................................... 570/247

* cited by examiner

Primary Examiner—Alan Siegel
(74) Attorney, Agent, or Firm—Rosenman & Colin LLP

(57) ABSTRACT

Using a process for the production of 1,2-dichloroethane by reacting ethylene and chlorine in the liquid phase in the presence of a catalyst, the 1,2-dichloroethane produced being drawn off in the gaseous phase, the high-boilers being separated from the 1,2-dichloroethane in a heavy-ends column and in a downstream vacuum column and the light-boilers and gases, such as ethylene and hydrogen, being separated in an EDC stripping column or in a light-ends column, a commercial-scale solution should be created to effectively remove the hydrogen chloride at the head of the stripping column or light-boiling column to avoid corrosion occurring there.

This is achieved in that the cleaned 1,2-dichloroethane leaving the heavy-ends column is cleaned in the EDC stripping column or in the light-ends column by separating the light-boilers and the gases. This is effected by using an alkaline substance to neutralize the vapors and/or the condensed vapors leaving the EDC stripping column or the light-ends column, the hydrogen chloride thus also being removed.

3 Claims, 1 Drawing Sheet

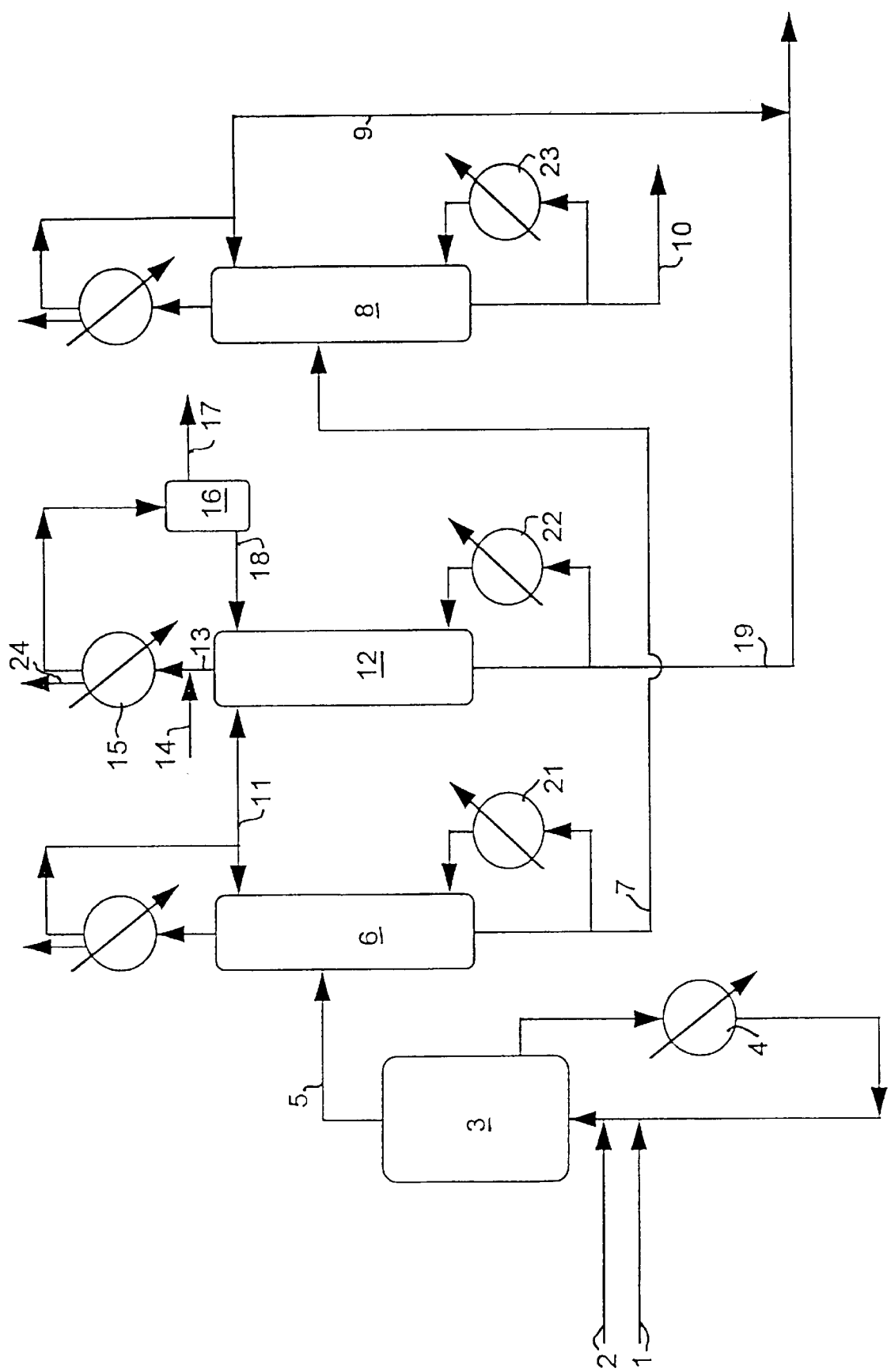

PROCESS FOR THE PRODUCTION OF 1, 2-DICHLOROETHANE

The invention involves a process for the production of 1,2-dichloroethane (EDC) by reacting ethylene and chlorine in liquid phase (direct chlorination) in the presence of a catalyst. The 1,2-dichloroethane produced is drawn off in the gaseous phase, high-boilers being separated from the 1,2-dichloroethane in a heavy-ends column and in a downstream vacuum column and the light-boilers and gases, such as ethylene and hydrogen, being separated in an EDC stripping column or in a light-ends column. 1,2-dichloroethane (EDC) is produced on a commercial scale by the direct chlorination of ethylene using chlorine gas. This reaction takes place under the influence of one or more catalysts and/or catalyst promoters in the liquid phase at temperatures of 75° C. to 100° C. and at pressures of 0.8 bar absolute to 3 bar absolute. During the course of this reaction the 1,2-dichloroethane produced is drawn off as a vapour and the resulting reaction enthalpy can be dissipated by boiling and condensing the 1,2-dichloroethane and recycling the condensed 1,2-dichloroethane stream from which the product itself has been removed. Alternatively, by cooling the boiling 1,2-dichloroethane sufficiently, it is possible to evaporate only the required amount of 1,2-dichloroethane produced. The cooling process is ideally effected by cooling the liquid phase which circulates in a forced or natural cycle. It is also possible to adjust the pressure in the reactor so that the 1,2-dichloroethane does not evaporate there, but is drawn off instead by the expansion and consequent partial evaporation of the circulating liquid 1,2-dichloroethane. This process step also involves the cooling of the liquid phase in a forced or natural cycle. The said 1,2-dichloroethane is cleaned by separating the high-boilers in a heavy-ends column and a downstream vacuum column and by separating the low-boilers and gases, such as ethylene and hydrogen chloride, in an EDC stripping column. The by-products obtained during the cleaning process are burnt and hydrogen chloride is recovered from the flue gases.

There are processes of this type in which gases and low-boilers are separated in a light-ends column. However, the concentration of water and hydrogen chloride occurring in the top of the column, the top-end condenser, the recycling vessel and the recycling pump causes considerable problems with corrosion and necessitates the use of extremely expensive construction materials which are still not entirely able to prevent the formation of $FeCl_3$. Processes for drying the vapours have not yet been perfected and do not function satisfactorily on a commercial scale.

Higher concentrations of $FeCl_3$ in 1,2-dichloroethane lead to increased coking in the cracking furnace and considerably reduce the service life with regard to the thermal cracking of 1,2-dichloroethane to produce vinyl chloride. In accordance with economic constraints, which lead cracking furnace operators to demand a service life of more than one year, the concentration of $Fe^{3+}$ in 1,2 dichloroethane must be below 0.5 ppm.

For this reason, the invention aims to use a technologically adequate process to create a commercial-scale solution which effectively removes the hydrogen chloride formed at the head of the EDC stripping or low-boiler column and thus prevents corrosion occurring there, and which complies with the specifications stipulated by cracking furnace operators for 1,2-dichloroethane.

The process, such as the one described in the introduction, fulfils this objective in that the cleaned 1,2-dichloroethane leaving the heavy-ends column is cleaned in the EDC stripping column or in the light-ends column thereby separating the light-boilers and the gases. This is effected by using an alkaline substance to neutralise the vapours and/or the condensed vapours leaving the EDC stripping column or the light-ends column, the hydrogen chloride thus also being removed.

This process method can also be used on a commercial scale to neutralise the hydrogen chloride at the head of the column and to then remove it effectively. As a result corrosion is prevented and the specifications stipulated by cracking furnace operators for 1,2-dichloroethane can be reliably met. This is a relatively low-cost process method thus permitting this process to be implemented economically on a commercial scale.

The preferred alkaline substance to be used is caustic soda solution.

In a further embodiment of the invention the neutralised vapours are condensed and then separated into an aqueous and an organic phase, the organic phase being returned to the EDC column. The organic phase can then be subjected to further treatment in the EDC column.

The invention is explained in more detail by the attached diagram showing a process flow diagram which represents the process step sequence in accordance with the invention.

A plant, in which the process for producing 1,2-dichloroethane in accordance with the invention can be implemented, has one direct chlorination reactor into which chlorine can be fed via line (1) and liquid ethylene via line (2). In reactor (3) 1,2-dichloroethane is produced from chlorine and ethylene at temperatures of 75° C. to 100° C. and pressures of 0.8 bar absolute to 3 bar absolute with the addition of one or more catalysts and/or catalyst promoters. The reaction heat occurring is dissipated via a heat exchanger (4) to such an extent that only the quantity of 1,2-dichloroethane produced is evaporated via line (5) into a heavy-ends column (6).

The column bottom inventory (7) in the heavy-ends column (6) contains 3 to 10% high-boilers which are fed via the column bottom discharge end into a vacuum column (8). The high-boilers are concentrated further in said vacuum column (8) and 1,2-dichloroethane is recovered at the head of the vacuum column (8) and carried off via line (9). The concentrated high-boilers are discharged via line (10) and are then burnt and hydrogen chloride is recovered.

The vapours produced are drawn off at the head of the heavy-ends column (6) via a vapours discharge outlet (11) and are fed into an EDC stripping column (12). The cleaned 1,2-dichloroethane is drawn off at the foot of this EDC stripping column (12) and piped off via a discharge outlet (19). The cleaned 1,2-dichloroethane stream, which constitutes the bottom discharge stream of the EDC stripping column, and the vapours discharge stream from the vacuum column (8) have a combined pipe system (lines 19 and 9).

The basic invention provides for the vapours forming in the EDC stripping column (12) to be carried off at the top via a vapour discharge (13) and then to be neutralised by adding caustic soda solution via a feed line (14). The vapours thus neutralised are then condensed in a condenser (15) before arriving in a recycle vessel (16). The aqueous phase is decanted in this recycle vessel (16), the outlet being shown as 17. The organic phase is recycled to the EDC stripping column via line (18).

The individual column evaporators (21, 22, 23) can also be heated by using the reaction heat from the direct chlorination in reactor 3. It goes without saying that the plant model previously described can be modified to implement the process without deviating from the object of the invention.

The following example serves to explain the invention even further. All temperatures are in degrees Celsius and all pressures are absolute. Wt/ppm means mg of a substance per kg total weight of 1,2-dichloroethane.

EXAMPLE

The EDC stripping column (12) was charged with a mass stream of 63,956 kg/h by withdrawing the vapours from the heavy-ends column. The stream had the following composition:

| | |
|---|---|
| 99.95 wt % | 1,2-dichloroethane |
| 150 wt/ppm | hydrogen chloride |
| 45 wt/ppm | ethylene |
| 100 wt/ppm | 1,1-dichloroethane |
| 125 wt/ppm | 1,1,2-trichloroethane |
| 15 wt/ppm | nitrogen |
| 8 wt/ppm | water |
| 8 wt/ppm | oxygen |
| 0.5 wt/ppm | $Fe^{3+}$ |

When the EDC stripping column (12) was in equilibrium conditions a temperature of 108° C. was reached by continuously drawing off 63,936 kg/h bottom product from the stripping column (12) at a pressure of 1.85 bar. At the top of the column 16,210 kg/h vapours were mixed with 58 kg/h caustic soda solution (with a sodium hydroxide concentration of 20% by wt.) at a pressure of 1.5 bar and at a saturated steam temperature of 98.6° C. The vapours condensed in the condenser (15) using cooling water and a refrigerating agent and flowed at a temperature of 45° C. into the recycle vessel (16). 73 kg/h aqueous phase were decanted, the organic phase was fed back to the column via the recycle line (18). 5 kg/h gases and non-condensed vapours were withdrawn via an outlet (24) (see diagram).

The EDC stripping column's bottom discharge (19) had the following composition:

| | |
|---|---|
| 99.98 wt %. | 1,2-dichloroethane |
| 0 wt/ppm | hydrogen chloride |
| 0 wt/ppm | ethylene |
| 55 wt/ppm | 1,1-dichloroethane |
| 125 wt/ppm | 1,1,2-trichloroethane |
| 0 wt/ppm | nitrogen |
| 3 wt/ppm | water |
| 0.5 wt/ppm | $Fe^{3+}$ |

It goes without saying that the above arrangement is only intended to be used for explanation purposes; the process in accordance with the invention can of course be used with other process conditions.

What is claimed is:

1. A process for the production of 1,2-dichlorethane (EDC), comprising the steps of:

(a) reacting ethylene and chlorine in liquid phase (direct chlorination) in the presence of a catalyst;

(b) drawing off 1,2-dichloroethane produced in gaseous phase;

(c) separating high-boilers from the 1,2-dichloroethane in a heavy-ends column and in a downstream vacuum column;

(d) separating light-boilers and gases including ethylene and hydrogen in an EDC stripping column or in a light-ends column; and (e) neutralizing vapors in the EDC stripping column or the light-ends column by using an alkaline substance, wherein the hydrogen chloride is removed and 1,2-dichloroethane leaving the heavy-ends column is cleaned in the EDC stripping column or in the light-ends column thereby separating the light boilers and the gases.

2. The process of claim 1, wherein caustic soda solution is used as the alkaline substance.

3. The process of claim 1, wherein the neutralized vapors are condensed and then separated into an aqueous and an organic phase, the organic phase being returned to the EDC column.

* * * * *